US00PP23515P2

(12) United States Plant Patent
Kordes

(10) Patent No.: US PP23,515 P2
(45) Date of Patent: Apr. 9, 2013

(54) CLIMBING ROSE PLANT NAMED 'KORTEMPORA'

(50) Latin Name: *Rosa hybrida*
Varietal Denomination: KORtempora

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 13/136,071

(22) Filed: Jul. 22, 2011

(51) Int. Cl.
*A01H 5/00* (2006.01)

(52) U.S. Cl. ..... Plt./115

(58) Field of Classification Search ..... Plt./112, Plt./109, 115
See application file for complete search history.

*Primary Examiner* — Kent L Bell

(57) ABSTRACT

A new and distinct variety of rose with long lasting, novel orange-red flowers, and attractive foliage with good disease resistance. It exhibits vigorous growth and an upright habit with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORtempora'.

CROSS REFERENCES AND FEDERAL R&D STATEMENT

There are no cross referenced or related applications. This variety was developed without the aid of any research grant.

BACKGROUND OF THE INVENTION

The present discovery constitutes a new and distinct variety of a garden rose plant which was discovered in a cultivated area in July, 2005. The new rose variety resulted from a naturally occurring mutation of unknown causation on a branch of 'KORromalu', a non-patented rose. The new rose plant was asexually propagated for evaluation. This new and distinctive garden rose variety is named 'KORtempora'.

SUMMARY OF THE INVENTION

The new rose plant may be distinguished from 'KORromalu', by the following combination of characteristics:

1. The color of 'KORtempora' is orange red while the color of 'KORromalu' is dark red.
2. The flower size of 'KORtempora' is medium while the flower size of 'KORromalu' is large.

The new and distinct rose plant was selected due to its:

1. Uniform growth and flowering;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORtempora' from all other varieties of which I am aware.

As part of the rose development program, Tim-Hermann Kordes asexually propagated the mutation by grafting and conducted evaluations and observations on the resulting plants in the inventor's nursery in Offenseth-Sparrieshoop, Germany. The first asexual propagation of 'KORtempora' was done by budding to seedling understocks in July, 2005 at the inventor's nursery in Offenseth-Sparrieshoop, Germany.

This initial and other subsequent propagations conducted in controlled environments demonstrate that 'KORtempora' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORtempora'.

DETAILED BOTANICAL DESCRIPTION

The following is a description of 'KORtempora', as observed growing in June, 2011 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORtersen', a non-patented rose variety from the same inventor is compared to 'KORtempora' in Chart 1.

CHART 1

| Characteristic | 'KORtempora' | 'KORtersen' |
|---|---|---|
| Flower color: | Orange red. | Dark pink. |
| Plant habit: | 180 cm (l) × 120 cm (w). | 150 cm (l) × 100 cm (w). |
| Number of flower petals: | Approximately 16. | Approximately 75. |

Parents:

*Parent*.—'KORromalu'.

Classification:

*Botanical classification*.—*Rosa hybrida* 'KORtempora'.

*Commercial classification*.—Climbing rose.

FLOWER AND FLOWER BUD

Blooming habit: Continuous.

Flower bud:

*Size*.—Upon opening, 25 mm in length from base of receptacle to end of bud and 20 mm diameter at its widest point.

*Bud form*.—Short. Pointed ovoid.

*Bud color*.—As sepals first unfold, bud color is Red Group 43B. When ¼ open, the upper surface of petals is Red Group 45B, and the lower surface is Red Group 43C. Guard petals are variable. Marginal zone: Red Group 45C. Middle zone: Mottled. Red Group 45C with Yellow-Green Group 145C and Green-White Group 157C.

*Sepals*.—Color: Upper surface Yellow-Green Group 146D suffused with Greyed-Purple Group 183C. Lower surface Yellow-Green Group 146A. Size: Average 27-30 mm (l)×9 mm (w). Shape: Weak foliaceous appendages on one or two of the five sepals. Quantity: Five. Apex: Apiculate. Base is flat at union with receptacle. Surface texture: Inner side: Moderately pubescent. Outer side: Glabrous with slight pubescence. Margins: Moderately pubescent with stipitate glands.

Receptacle:

*Surface*.—Glabrous to slightly pubescent at base.

*Color*.—Yellow-Green Group 144A. suffused with Greyed-Purple Group 183C.

*Shape*.—Urn-shaped.

*Size*.—8-9 mm (h)×7 mm (w).

Peduncle:

*Surface*.—With fine hairs and stipitate glands.

*Length*.—25-30 mm average length.

*Diameter*.—2-3 mm average diameter.

*Color*.—Greyed-Red Group 182C to Greyed-Red Group 183A.

*Strength*.—Somewhat strong.

*Borne*.—Multiple flower buds per stem, generally 2 to 5.

Flower bloom:

*Fragrance*.—None.

*Duration*.—On the plant 4-5 days. As a cut flower, 3-4 days. Senesced petals drop away cleanly.

*Size*.—Medium sized for a. climbing rose. When open, the average flower diameter is between 60 to 85 mm and the average flower height is 10 to 12 mm.

*Form*.—Shape of flower when viewed from the side: Upon opening, upper part: Flat. Upon opening, lower part: Flattened convex. Open flower, upper part: Flat. Open flower, lower part: Concave.

Color:

*Upon opening, petals*.—Outermost petals: Outer Side: Red Group 46C. Inner Side: Red Group 44A to 45A. Innermost petals: Outer Side: Red Group 45B. Inner Side: Red Group 45B.

*Upon opening, basal petal spots*.—Basal petal spot, outermost petals: Outer Side: White Group 155C. Inner Side: White Group 155B. Basal petal spot, innermost petals: Outer Side: White Group 155C. Inner Side: White Group 155D.

*After opening, petals*.—Outermost petals: Outer Side: Red Group 45C. Inner Side: Red Group 45B. Innermost petals: Outer Side: Red Group 45C. Inner Side: Red Group 45B.

*After opening, basal petal spots*.—Basal petal spot, outermost petals: Outer Side: White Group 155C. Inner Side: White Group 155D. Basal petal spot, innermost petals: Outer Side: White Group 155D. Inner Side: White Group 155C.

General tonality: On open flower Red Group 45B. No change in the general tonality at the end of the 5$^{th}$ day. Afterwards, general tonality is Red Group 46B.

Petals:

*Petal count*.—Semi-double. Approximately 16 petals under normal conditions.

*Petal reflex*.—Limited reflex.

*Petal margin*.—Mucronate.

*Petal shape*.—Obtuse. Apex shape is obtuse. Shape of base is deltoid.

*Petal size*.—Outer petal: 35 mm (l)×30 mm (w). Inner petal: 30 mm (l)×20 mm (w).

*Thickness*.—Thin.

*Petal arrangement*.—Not formal.

Petaloids: Present.

*Petaloid count*.—Average of 0-4 per flower.

*Petaloid size*.—Petaloids are 20-25 mm (l) and 4-5 mm wide on average.

*Petaloid color*.—Color of inner side is Red Group 45B. Color of outer side is Red Group 45B.

*Petaloid texture*.—Smooth.

*Margins*.—Entire.

*Petaloid shape*.—Irregular ranging from obovate to subulate. Apex is cuneate. Base is acicular.

Reproductive organs:

*Pistils*.—Few. Approximately 10 present. Stigmas: Location: Slightly inferior in position to anthers. Color: Yellow-Orange Group 18B. Styles: Length: Approximately 4 mm long. Color: Yellow-Green Group 145C.

*Stamens*.—Approximately 30 on average and regularly arranged. Anthers: Size: Average 1 mm long. Pollen: Generally present. Color: Greyed-Orange Group 164B. Filaments: Color: Red Group 53B and 53C. Length: 5 mm.

THE PLANT

*Growth*.—Vigorous.

*Plant habit*.—Upright climbing habit. When grown as a budded field plant the average plant height is 180 cm and the average plant width is 120 cm.

Stems:

*Stem color*.—Young wood: Yellow-Green Group 146C. Older wood: Yellow-Green Group 146D.

*Stem surface*.—Young wood: Smooth. Older wood: Smooth.

Prickles: Present.

*Incidence*.—Approximately 6 prickles per each 10 cm of stem.

*Size*.—Average length: 5 mm.

*Color*.—Immature prickles: Greyed-Red Group 178A. Mature prickles: Greyed-Purple Group 183B. Senescing to Greyed-Orange Group 165A.

*Shape*.—Concave.

Leaves and leaflets: Normally 5 leaflets on normal leaves in middle of the stem.

*Venation pattern*.—Pyramidal net pattern.

*Leaf size:* 100 mm (l)×75 mm (w).

*Quantity*.—Abundant.

*Texture*.—Upper side of leaflet: Semi glossy. Smooth. Under side of leaflet: Matte. Smooth.

*Color, mature foliage*.—Upper Leaf Surface: Green Group 137A. Lower Leaf Surface: Green Group 137C.

*Color, juvenile foliage*.—Upper Leaf Surface: Yellow-Green Group 146B. Lower Leaf Surface: Yellow-Green Group 148B.

*Anthocyanin*.—Present. Intonations present on juvenile leaf margins and developing leaves. Greyed-Purple Group 183C.

Stipules:

*Size*.—Average 25 mm (l). Average 5 mm (w) between the tips of the stipules.

*Stipule color*.—Green Group 137C.

*Anthocyanin*.—Greyed-Purple Group 183C.

*Margins*.—Limited stipitate glands.

*Shape*.—Apex: Aristate. Base: Slightly winged.

Petiole:

*Length*.—Average 20 mm.

*Diameter*.—Average 2 mm.

*Petiole color*.—Yellow-Green Group 146C. Suffused with Greyed-Purple Group 183D on the upper side.

*Underneath*.—Smooth.

*Margins*.—Ridged with limited numbers of stipitate glands.

Petiole rachis:

*Length*.—Average 8-10 mm.

*Diameter*.—Average 2 mm.

*Color*.—Yellow-Green Group 146C.

*Anthocyanin*.—Present on upper side of juvenile tissue. Greyed-Purple Group 183C and 183D.

*Underneath*.—Smooth with an occasional prickle at point of leaflet attachment.

*Margins*.—With stipitate glands.

*Stipitate glands*.—Limited numbers of stipitate glands on margins.

Leaflets:

*Size*.—Average size of the terminal leaflet is 55 mm (l)×35 mm (w).

*Shape*.—Entire leaflet: Ovate. Base: Obtuse. Apex: Cuspidate.

*Margins*.—Finely serrated.

*Texture*.—Upper side: Semi-glossy. Smooth. Under side: Matte. Smooth.

Hips/seed formation: None observed.

Winter hardiness: To date, the variety has been grown successfully in Zones 5-9.

Disease resistance: Excellent resistance to powdery mildew (*Sphaerotheca pannosa*), blackspot (*Diplocarpon rosae*), and rust (*Phragmidium* sp.) diseases under normal growing conditions.

I claim:

1. A new and distinct variety of rose plant, as described and illustrated herein.

* * * * *

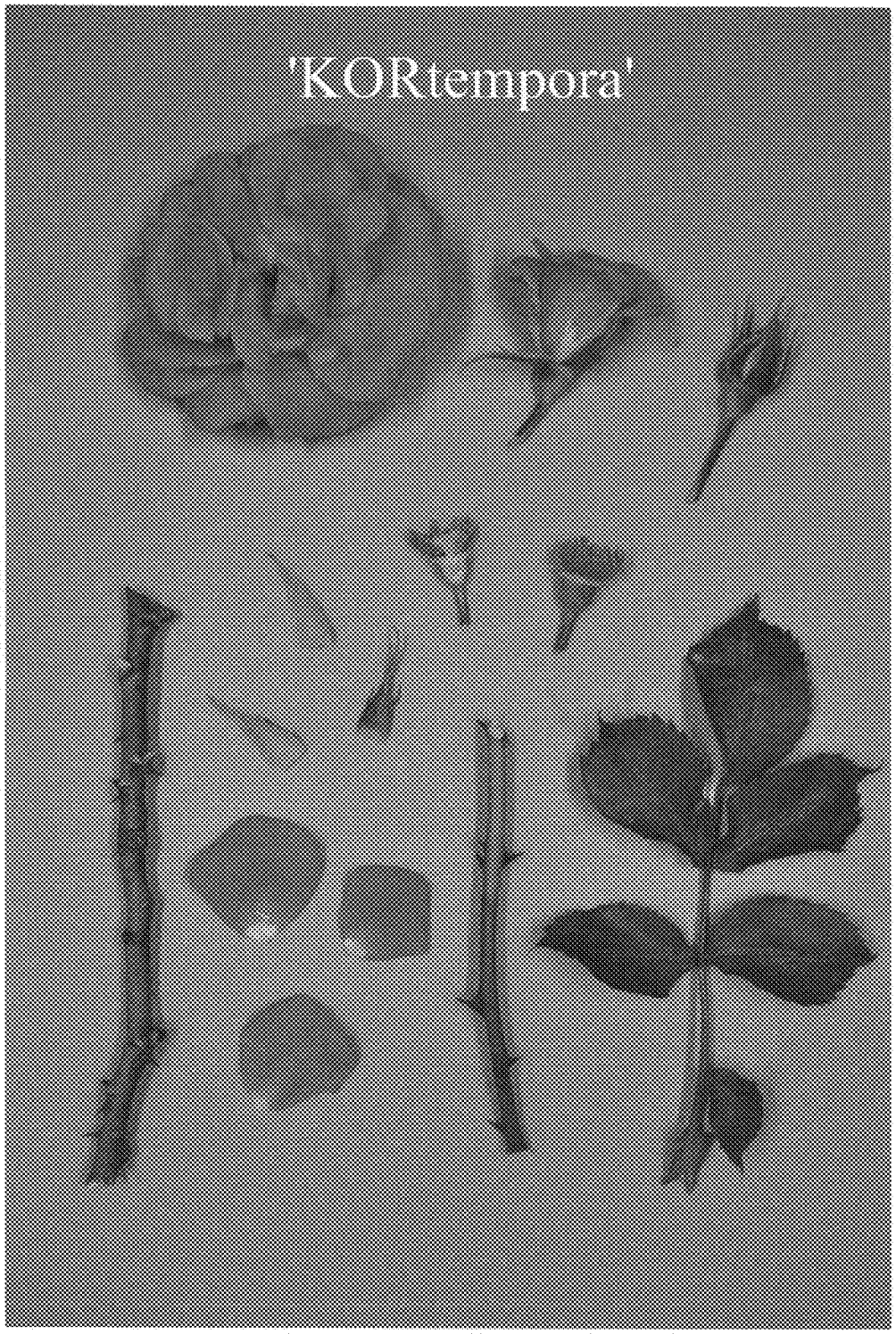
'KORtempora'